United States Patent [19]

Polyakov et al.

[11] 4,300,007
[45] Nov. 10, 1981

[54] METHOD FOR PREPARING $C_3$-$C_4$ OLEFINS AND VINYLAROMATIC COMPOUNDS

[76] Inventors: Sergei A. Polyakov, 3 Sovetskaya ulitsa, 16, kv. 9; Aron L. Shapiro, ulitsa Lensoveta, 50, kv. 29, both of Leningrad, U.S.S.R.

[21] Appl. No.: 839,552

[22] Filed: Oct. 5, 1977

[51] Int. Cl.$^3$ .............................................. C07C 4/06
[52] U.S. Cl. .................................. 585/323; 585/439; 585/445
[58] Field of Search ...................... 260/668 B, 669 R; 585/323, 439, 445

[56] References Cited

U.S. PATENT DOCUMENTS

| | | | |
|---|---|---|---|
| 2,110,833 | 3/1938 | Mark et al. | 260/669 R |
| 2,369,281 | 2/1945 | Chavey | 260/669 R |
| 2,416,990 | 3/1947 | Gorin et al. | 260/669 R |
| 2,441,095 | 5/1948 | Cheney et al. | 260/669 R |
| 2,449,004 | 9/1948 | Morrell et al. | 260/669 R |
| 2,728,802 | 12/1955 | Closson et al. | 260/668 B |
| 2,939,889 | 7/1960 | Amos et al. | 260/669 R |
| 3,449,455 | 6/1969 | Napolitano et al. | 260/668 B |

*Primary Examiner*—Delbert E. Gantz
*Assistant Examiner*—Joseph A. Boska
*Attorney, Agent, or Firm*—Burton L. Lilling

[57] ABSTRACT

A method for preparing $C_3$-$C_4$ olefins and vinylaromatic compounds, viz. styrene, vinyltoluenes or vinylxylenes which comprises alkylation of toluene or methyl derivatives thereof with a $C_2$-$C_3$ olefin into the methyl group. The resulting alkylaromatic compounds are subjected to conversion to the desired products in the presence of ethylene on a catalyst consisting of chromium oxide, tungsten oxide and an oxide of an alkali or alkali-earth metal supported by a carrier.

The method according to the present invention makes it possible to increase the yield of vinylaromatic compounds, obtain individual isomers of vinyltoluene or vinylxylene and efficiently utilize the part of the alkyl radical of the alkylaromatic compound lost in the prior art method.

3 Claims, No Drawings

METHOD FOR PREPARING C₃-C₄ OLEFINS AND VINYLAROMATIC COMPOUNDS

FIELD OF THE INVENTION

The present invention relates to the art of petrochemical synthesis and, more specifically, to a method for preparing $C_3$-$C_4$ olefins and vinylaromatic compounds, viz. styrene, vinyltoluenes or vinylxylenes.

Styrene is one of the primary monomers employed for the production of a synthetic rubber and plastics. Vinyltoluene and vinylxylenes are extensively used for the production of polymeric materials for special applications. $C_3$-$C_4$ olefins find an extensive application in a whole range of petrochemical processes.

BACKGROUND OF THE INVENTION

Known in the art is a method for preparing vinylaromatic monomers such as styrene, vinyltoluenes or vinylxylenes by way of alkylation of benzene, toluene or xylene with ethylene into the ring, followed by dehydrogenation of the resulting alkylaromatic compounds. The alkylation is conducted at a temperature within the range of from 50° to 120° C., under a pressure of up to 10 atm in the presence of aluminum chloride or sulphuric acid. The dehydrogenation is performed at a temperature within the range of from 500° to 700° C. under atmospheric pressure on a heterogeneous catalyst. The yield of vinylaromatic compounds is as high as 80% by weight.

This prior art method has a disadvantage residing in that it makes possible to produce merely a mixture of isomers of vinyltoluene or vinylxylene which is impossible to separate for further economically efficient utilization thereof.

Also known in the art is a method for preparing styrene by way of heating monoalkylbenzene to a temperature within the range of from 550° to 800° C. in the presence of a sulphur-organic compound or a halogenalkyl.

As the monoalkylbenzenes use can be made of compounds of the formula: $C_6H_5$—$CH_2$—$CH_2$—R (i.e. propyl-, butyl-, pentylhexyl-, or heptylbenzene).

Thus, upon passing butylbenzene through a steel pipe at a temperature of 600° C. in the presence of thiophenol, styrene is formed with a selectivity of 75.1 mol.% (58.2% by weight) compared to 55.6 mol.% in the absence of thiophenol.

Monoalkylbenzenes used for conversion to styrene are produced by alkylation of toluene into the methyl group by means of olefins.

This prior art method also has a disadvantage residing in a low selectivity of conversion of monoalkylbenzene to styrene (58.2 mol.%). Furthermore, in this prior art method a part of the alkyl radical is split-off in the form of light paraffin hydrocarbons (methane, ethane and the like) which cannot be efficiently employed.

SUMMARY OF THE INVENTION

It is an object of the present invention to increase the yield of vinylaromatic compounds.

It is another object of the present invention to prepare styrene or individual isomers of vinyltoluene or vinylxylene simultaneously with the preparation of $C_3$-$C_4$ olefins.

These and other objects of the present invention are accomplished by that in a process for preparing $C_3$-$C_4$ olefins and vinylaromatic compounds, viz. styrene, vinyltoluenes or vinylxylenes by alkylation of toluene or methyl derivatives thereof by a $C_2$-$C_3$ olefin in the methyl group, followed by conversion of the resulting alkylaromatic compounds to the desired product. In accordance with the present invention the conversion of the alkylaromatic compounds is conducted in the presence of ethylene using a catalyst consisting of the following components, percent by weight:

chromium oxide: 3.0 to 16.1
tungsten oxide: 2.0 to 8.5
oxide of an alkali
or
alkali-earth metal: 0.1 to 3.0
silica
or
alumosilicate: the balance.

DETAILED DESCRIPTION OF THE INVENTION

The method according to the present invention is performed in the following manner. Toluene or its methyl derivatives (xylenes, trimethylbenezenes) are subject to alkylation with ethylene or propylene into the methyl group in the presence of a basic catalyst. The alkylation is conducted at a temperature within the range of from 50° to 250° C. under a pressure of up to 50 atm.g. in the presence of an alkali metal or an organometallic compound as a catalyst.

The alkylaromatic compounds resulting from this alkylation are subjected to conversion at a temperature within the range of from 400° to 700° C. at atmospheric or above atmospheric pressure (up to 50 atm.g.) in the presence of ethylene using a heterogeneous catalyst.

The ratio between the alkylaromatic compounds and ethylene can be varied within an indefinite range. The technologically optimal ratio ranges from 1:5 to 1:15 which is associated with recycling of ethylene.

The catalyst for the conversion is prepared by depositing oxides of chromium, tungsten and an oxide of an alkali or alkali-earth metal in an appropriate ratio on a carrier such as silica or alumosilicate. The best results are obtained with the following content of the components, percent by weight:

chromium oxide: 3.0 to 16.1
tungsten oxide: 2.0 to 8.5
oxide of an alkali
or
alkali-earth metal: 0.1 to 3.0
silica or alumosilicate: the balance.

Owing to the method according to the present invention, the yield of vinylaromatic compounds is made as high as 70 to 75% by weight calculated for the converted alkylaromatic compounds.

The method according to the present invention also makes it possible to obtain individual isomers of vinyltoluene or vinylxylene which has been hitherto unobtainable in none of the prior art methods.

The method according to the present invention also enables the production of $C_3$-$C_4$ olefins simultaneously with the vinylaromatic compounds, wherein the portion of the alkyl radical of alkylaromatic compounds previously lost in the prior art methods can be now utilized with higher economic efficiency.

For a better understanding of the present invention, given hereinbelow are some specific examples illustrating the process for preparing $C_3$-$C_4$ olefins and vinylaromatic compounds, viz. styrene, vinyltoluenes or vinylxylenes.

EXAMPLE 1

Charged into an autoclave are 184 g of toluene, 45 g of propylene and 2 g of metallic potassium. The mixture is maintained for 2 hours under stirring at a temperature of 198° C. Conversion of propylene is 60%. The yield of isobutylbenzene is 62 g which corresponds to 83.4% by weight as calculated for the converted propylene and toluene. 60 g of isobutylbenzene recovered by rectification from the alkylation products are subjected to a catalytic conversion in a mixture with 110 g of ethylene at a temperature of 456° C., space velocity of 187 hr$^{-1}$ on a catalyst consisting of 3.0% by weight of $Cr_2O_3$, 4.3% by weight of $WO_3$, 1.8% by weight of $K_2O$ supported on alumosilicate. As a result of the conversion there are obtained, g: $H_2$-0.1; $CH_4$-0.8; $C_2H_2$-1.2; $C_3H_6$-0.2; $C_4H_8$-6.0; benzene-0.2; toluene-0.6; ethylbenzene-0.8; styrene-12.7; isobutylbenzene-0.6; high-boiling products-0.5. Conversion of isobutylbenzene is 32.4%. The yield of styrene is 65.4% by weight as calculated for the converted isobutylbenzene. Total yield of styrene and isobutylene is 78.9% by weight as calculated for the converted isobutylbenzene and ethylene, and 67.2% by weight as calculated for the converted toluene, propylene and ethylene.

EXAMPLE 2

Charged into an autoclave are 184 g of toluene, 30 g of ethylene and 4 g of benzylsodium. The mixture is maintained for two hours under stirring at a temperature of 180° C. The conversion of toluene is 34.5%. The yield of propylbenzene is 64.3 g which corresponds to 83.3% by weight as calculated for the converted ethylene and toluene. 60 g of propylbenzene recovered by rectification from the alkylation products are subjected to a catalytic conversion in a mixture with 95 g of ethylene at a temperature of 704° C., space velocity of 684 hr$^{-1}$ on a catalyst consisting of 6.2% by weight of $WO_3$, 5.4% by weight of $Cr_2O_3$; 0.1% by weight of $Na_2O$; 2.3% by weight of $Al_2O_3$; 86% by weight of $SiO_2$.

As a result of the conversion there are obtained (g): $H_2$-0.2; $CH_4$-1.8; $C_2H_6$-2.7; $C_3H_6$-5.4; $C_4$–$C_5$ hydrocarbons-0.4; benzene-0.8; toluene-3.4; ethylbenzene-2.3; styrene-15.6; high-boiling products 0.9. The conversion of propylbenzene is 41.4%. The total yield of propylene and styrene is 84.9% by weight as calculated for the converted propylbenzene and ethylene. The total yield of styrene and propylene is 70.6% by weight as calculated for the converted toluene and ethylene.

EXAMPLE 3

Charged into an autoclave are 212 g of ortho-xylene and 2 g of metallic potassium; ethylene is then admitted into the reactor to a pressure of 30 atm.g. and the mixture is maintained for one hour at a temperature of 180° C. under stirring.

Xylene conversion is 23%. As a result of the reaction there are obtained 54 g of ortho-methylpropylbenzene. The yield is 83.2% by weight (the balance being heavier alkylaromatic compounds). 50 g of ortho-methylpropylbenzene recovered by rectification from the alkylation products are subjected to a catalytic conversion in a mixture with 100 g of ethylene at a temperature of 510° C., space velocity of 485 hr$^{-1}$ on a catalyst containing, percent by weight: 4% of $Cr_2O_3$; 8.5% of $WO_3$, 0.8% of $K_2O$ supported on alumosilicate.

The conversion gives the following compounds, (g): $H_2$-0.2; $CH_4$-0.2; $C_2H_6$-0.8; $C_3H_6$-3.9; $C_3H_8$-0.1; hydrocarbons $C_4$-$C_6$-0.1; toluene-0.3; ethylbenzene and xylenes-0.6; styrene-0.5; methylstyrene-10.1; high-boiling products-0.3. Conversion of methylpropylbenzene is 27%. The yield of methylstyrene is 75.1% by weight as calculated for the converted methylpropylbenzene. The total yield of propylene and methylstyrene is 82.3% by weight as calculated for the converted methylpropylbenzene and ethylene, and 68.5% by weight as calculated for the reacted xylene and ethylene. The methylstyrene recovered by rectification contains 97% by weight of the ortho-isomer.

EXAMPLE 4

Charged into autoclave are 212 g of para-xylene, 3.9 g of metallic potassium and 63 g of propylene and the mixture is maintained at a temperature of 205° C. for 3.5 hours under stirring. Conversion of xylene is 34.2%. As a result of the reaction there are obtained 82 g of para-methylisobutylbenzene. The yield is 71.2% by weight (the balance being represented by heavier alkylaromatics). 80 g of paramethyl-isobutylbenzene recovered by rectification from the alkylation products are subjected to a catalytic conversion in a mixture with 150 g of ethylene at a temperature of 485° C., space velocity of 210 hr$^{-1}$ on a catalyst consisting of the following components, percent by weight: 16.1 of $Cr_2O_3$; 7.2 $WO_3$; 0.2 $K_2O$; 76.5 $SiO_2$. As a result of the conversion there are obtained (g): $H_2$-0.2; $CH_4$-0.4; $C_2H_6$-0.9; $C_3H_6$-0.8; $C_3H_8$-0.1; $C_4H_8$-8.4; hydrocarbons $C_5$-$C_6$-0.2; toluene-0.9; xylenes-1.1; styrene-0.5; methylstyrene-17.1; high-boiling products-0.4. Conversion of methyl-isobutylbenzene is 31.1%. The yield of methylstyrene is 68.5% by weight as calculated for the converted methyl-isobutylbenzene. The total yield of isobutylene and methylstyrene is 82.5% by weight as calculated for the converted methyl-isobutylbenzene and ethylene and 59.1% by weight for the converted xylene, propylene and ethylene. The methylstyrene recovered by rectification contains 98% of the para-isomer.

EXAMPLE 5

Charged into an autoclave are 180 g of 1,3,5-trimethylbenzene, 3.5 g of metallic potassium; ethylene is then fed thereinto to a pressure of 30 atm.g. and the mixture is maintained for 1.5 hour at a temperature of 170° C. under stirring. Conversion of 1,3,5-trimethylbenzene is 28.4%. As a result of the reaction there are obtained 52 g of 3.5-dimethyl propylbenzene. The yield of the product is 82.5% by weight (the balance being represented by products of polyalkylation with ethylene). 50 g of 3,5-dimethylpropylbenzene recovered by rectification from the alkylation products are subjected to a catalytic conversion in a mixture with 100 g of ethylene at a temperature of 520° C., space velocity of 190 hr$^{-1}$ on a catalyst consisting of the following components, percent by weight: $Cr_2O_3$-5.1; $WO_3$-2.0; $Al_2O_3$-44.8; $SiO_2$-45.2; MgO-2.9.

As a result of the conversion there are obtained (g): $H_2$-0.2; $CH_4$-0.5; $C_2H_6$-0.9; $C_3H_6$-3.8; $C_3H_8$-0.1; $C_4$–$C_6$ hydrocarbons-0.1; toluene-0.2; xylenes-0.2; methylstyrene-0.1; trimethylbenzene-0.4; dimethylstyrene-10.8; high-boiling products-0.2. Conversion of dimethylpropylbenzene is 28.2%. The yield of dimethylstyrene is 76.6% by weight as calculated for the converted dimethylpropylbenzene. The total yield of proylene and dimethylstyrene is 83.3% by weight as calculated for the converted dimethylpropylbenzene and ethylene and 69.2% by weight of calculated for the converted trimethylbenzene and ethylene. The dimethylstyrene recovered by rectification contains 95% of 3.5-dimethylstyrene.

What is claimed is:

1. A method for preparing $C_3$–$C_4$-olefins and vinylaromatic compounds selected from the group consisting of styrene, vinyltoluenes and vinylxylenes comprising alkylation of aromatic hydrocarbons of the benzene series selected from the group consisting of toluene and methyl derivatives of toluene, by means of a $C_2$–$C_3$ olefin into the methyl group, followed by conversion of the resulting alkylaromatic compounds to the desired products in the presence of ethylene using a catalyst consisting of the following components, percent by weight:

chromium oxide: 3.0 to 16.1
tungsten oxide: 2.0 to 8.5
an oxide selected from the group consisting of an oxide of alkali metal and an oxide of an alkali-earth metal: 0.1 to 3.0
a carrier selected from the group consisting of silica and alumosilicate: the balance.

2. The method of claim 1, wherein the alkylation is conducted at a temperature of 50°–250° C. and a pressure of up to 50 atm.g.

3. The method of claim 1, wherein the ratio of alkylaromatic compounds and ethylene varies from 1:5 to 1:15, respectively.

* * * * *